US008735374B2

(12) United States Patent
Zerbe et al.

(10) Patent No.: US 8,735,374 B2
(45) Date of Patent: May 27, 2014

(54) ORAL MUCOADHESIVE DOSAGE FORM

(75) Inventors: Horst G. Zerbe, Hudson (CA); Nadine Paiement, Ville St. Laurent (CA)

(73) Assignee: Intelgenx Corp., Quebec (CA)

( * ) Notice: Subject to any disclaimer, the term of this patent is extended or adjusted under 35 U.S.C. 154(b) by 640 days.

(21) Appl. No.: 12/836,810

(22) Filed: Jul. 15, 2010

(65) Prior Publication Data

US 2011/0028431 A1 Feb. 3, 2011

Related U.S. Application Data

(60) Provisional application No. 61/230,504, filed on Jul. 31, 2009.

(51) Int. Cl.
*A61K 31/724* (2006.01)
*A61K 31/715* (2006.01)
*A61P 27/06* (2006.01)
*A61P 25/06* (2006.01)
*A61P 25/08* (2006.01)
*A61P 11/06* (2006.01)

(52) U.S. Cl.
USPC ............................... 514/58; 514/54; 536/103

(58) Field of Classification Search
USPC ...................................... 514/58, 54; 536/103
See application file for complete search history.

(56) References Cited

U.S. PATENT DOCUMENTS

| | | | |
|---|---|---|---|
| 4,572,832 A | 2/1986 | Kigasawa et al. | |
| 4,900,552 A | 2/1990 | Sanvordeker et al. | |
| 6,248,363 B1 | 6/2001 | Patel et al. | |
| 6,267,985 B1 | 7/2001 | Chen et al. | |
| 6,287,603 B1 | 9/2001 | Prasad et al. | |
| 6,383,513 B1 | 5/2002 | Watts et al. | |
| 6,566,504 B2 | 5/2003 | Bhattacharya et al. | |
| 6,569,463 B2 | 5/2003 | Patel et al. | |
| 6,730,330 B2 | 5/2004 | Whittle et al. | |
| 6,761,903 B2 | 7/2004 | Chen et al. | |
| 6,884,790 B2 | 4/2005 | Pitha | |
| 6,923,988 B2 | 8/2005 | Patel et al. | |
| 6,958,326 B2 | 10/2005 | Backensfeld et al. | |
| 7,025,998 B2 | 4/2006 | Senin et al. | |
| 7,423,026 B2 | 9/2008 | Jarvinen et al. | |
| 7,592,328 B2 | 9/2009 | Jarho et al. | |
| 2003/0003113 A1* | 1/2003 | Lewandowski | 424/400 |
| 2005/0244502 A1* | 11/2005 | Mathias et al. | 424/487 |
| 2006/0034937 A1 | 2/2006 | Patel | |
| 2006/0160888 A1 | 7/2006 | Kottayil et al. | |
| 2007/0104741 A1 | 5/2007 | Murty et al. | |

FOREIGN PATENT DOCUMENTS

CN 101396364 A * 4/2009
WO 9932107 7/1999

OTHER PUBLICATIONS

Mannila et al. (European Journal of Pharmaceutical Sciences 26 (2005) 71-77).*
Guo et al.; CN101396364 A; Apr. 1, 2009 (English Machine Translation).*
STN abstract of Guo et al.; CN101396364 A; Apr. 1, 2009 (abstract sent).*
Munjal et al. "Polymeric Systems for Amorphous Δ9—Tetrahydrocannabinol Produced by a Hot-Melt Method. Part II: Effect of Oxidation Mechanisms and Chemical Interactions on Stability," Journal of Pharmaceutical Sciences, vol. 95, No. 11, Nov. 2006.
Munjal et al. "Chemical Stabilization of a Δ9—Tetrahydrocannabinol Prodrug in Polymeric Matrix Systems Produced by a Hot-Melt Method: Role of Microenvironment pH," AAPS PharmSciTech 2006; 7 (3) Article 71.
Hirayama et al., "Cyclodextrin-based Controlled Drug Release System," Advanced Drug Delivery Reviews 36, 1999, pp. 125-141.

* cited by examiner

*Primary Examiner* — Shaojia Anna Jiang
*Assistant Examiner* — Michael C Henry
(74) *Attorney, Agent, or Firm* — Butzel Long

(57) ABSTRACT

A direct compression formulation suitable for preparing buccal and/or sublingual and dosage forms incorporates a combination of a non-ionic polymeric solubility enhancer, a mucoadhesive polymer, a filler, a disintegrant, and a pharmaceutically active agent. Cannabinoid-cyclodextrin complexes exhibiting an improved property selected from improved stability, higher product yield and improved product uniformity may be obtained by complexing the cannabinoid with the cyclodextrin in a liquid medium containing an antioxidant. To enhance stability, product yield and/or product uniformity, complexing may be done while the liquid medium is in contact with an atmosphere having a very low oxygen content. The resulting complexes may be combined with decomplexing agents and/or dispersed in a matrix material comprised of a hydrogel-forming polymer to provide enhanced absorption of the cannabinoid through oral mucosa and reduced ingestion of the cannabinoid as compared with known commercially available cannabinoid-containing oral dosage forms.

8 Claims, No Drawings

ORAL MUCOADHESIVE DOSAGE FORM

CROSS REFERENCE TO RELATED APPLICATION

This application claims priority to U.S. Provisional Application No. 61/230,504, filed on Jul. 31, 2009, and entitled DOSAGE FORMS OF COMPLEXED CANNABINOIDS, the entire contents of which are hereby incorporated herein by reference.

FIELD OF THE INVENTION

This invention relates to oral pharmaceutical dosage forms and more particularly to oral dosage forms in which a substantial portion of the active ingredient is released in the oral cavity for oral adsorption.

This invention also relates to oral pharmaceutical dosage forms and more particularly to buccal and/or sublingual oral dosage forms comprised of at least one pharmaceutically active cannabinoid complexed with cyclodextrin.

BACKGROUND OF THE INVENTION

Buccal and sublingual oral dosage forms are dosage forms that are intended to be held in the mouth or under the tongue until they have completely dissolved. Unlike most oral dosage forms in which the pharmaceutically active ingredient is delivered to the gastrointestinal tract of the patient for absorption of the drug through the stomach or intestinal epithelium, sublingual and/or buccal dosage forms are designed to release the pharmaceutically active ingredient in the mouth for absorption through oral mucosa. Buccal dosage forms are intended to be inserted into the buccal pouch (a space generally defined between a cheek and the gums) and dissolve or erode relatively slowly, whereas sublingual oral dosage forms are intended to be held under the tongue and dissolve more rapidly. As a result, buccal dosage forms, including mucoadhesive formulations, are generally formulated with excipients to optimize drug release into and through oral mucosa and to minimize release of the drug into the gastrointestinal tract. Otherwise, buccal and sublingual dosage forms are substantially similar, the differences being more a matter of degree than of kind.

Sublingual and/or buccal oral dosage forms are preferred for delivering certain pharmaceutically active agents to the bloodstream. For example, many pharmaceutically active agents that are metabolized in the small intestine and/or liver (pharmaceutically active agents exhibiting what is known as "the first pass effect") can be more effectively administered sublingually or buccally through oral mucosal tissue.

Sublingual and/or buccal oral dosage forms also may provide a faster onset of therapeutic effect and/or improved bioavailability of certain pharmaceutically active agents that can be absorbed through the oral mucosa, thereby bypassing gastrointestinal and hepatic metabolism processes. In addition, such dosage forms may be preferred for administering certain pharmaceutically active agents to achieve better patient acceptance and compliance, especially among those patients that have difficulty swallowing. Buccal and/or sublingual dosage forms may also be employed in some cases to overcome problems with pharmaceutically active agents that are poorly absorbed from the gastrointestinal tract and which may not be effectively administered transdermally, subcutaneously or intravenously.

A known problem with transmucosal administration via buccal and/or sublingual dosage forms is that pharmaceutically active agents, especially those that are not rapidly absorbed through oral mucosa may be washed away in substantial proportion because of the continuous secretion of saliva in the oral cavity. Suitable buccal and/or sublingual dosage forms must remain in contact with oral mucosa for a time sufficient for absorption of a pharmaceutically active agent that is capable of being absorbed through oral mucosa. More specifically, the dosage form must not dissolve and/or disintegrate at such a rapid rate that an undesirably high proportion of the pharmaceutically active ingredient is washed away by saliva into the gastrointestinal tract. However, the rate of disintegration or dissolution of the dosage form must not be so slow as to cause discomfort or inconvenience for the patient, which often leads to non-compliance or poor compliance with a prescribed dosage regimen. Similarly, suitable buccal and/or sublingual dosage forms should be of a size and shape that avoids discomfort to the patient during use, or which leaves a gritty or other undesirable feeling in the mouth.

Cannabinoids include a class of terpenophenoic compounds commonly derived from the cannabis sativa plant, which is commonly known as marijuana. Cannabinoids encompass a variety of compounds structurally related to tetrahydrocannabinol (THC) which can bind to cannabinoid receptors.

Actual or potential therapeutic applications for cannabinoids such as THC include the treatment of multiple sclerosis and other forms of muscular spasm, migraine headache, glaucoma, asthma, inflammation, insomnia, high blood pressure, nausea and vomiting. Other potential therapeutic applications include the use of cannabinoids as oxytoxic, anxiolytic, anti-convulsive, anti-depressive, anti-psychotic, and anti-cancer agents. Cannabinoids have also been used as appetite stimulants.

Oral pharmaceutical dosage forms are generally preferred, relative to other forms, because the oral dosage forms are generally more easily administered, cause less patient discomfort, and achieve greater patient compliance with a prescribed therapeutic regimen. A commercially available product, sold as Marinol® soft gelatin capsules, contains $\Delta^9$-tetrahydrocannabinol (THC), also known as dronabinol, as the active ingredient. This product has been approved by the Food and Drug Administration for the control of nausea and vomiting associated with chemotherapy and for appetite stimulation in AIDS patients suffering from wasting syndrome. In the Marinol® dosage form, the active agent is dissolved in sesame oil and encapsulated in a gelatin shell for oral administration. However due to the combined effect of first pass hepatic metabolism, high lipid solubility and low water solubility, only about 10-20% of an administered dose reaches systemic circulation. In addition, there is variability in the maximum or peak concentration of the active agent in the blood plasma between administered dosages. It has also been found that fasting or food deprivation may decrease absorption of THC from the dosage form, and that there is a large inter-subject variability in the amount of THC absorption from the dosage form.

The actual and/or potential utility of cyclodextrin/cannabinoid complexes is recognized in the art. For example, Shoyama (J. Natural Products, 46:5 633-637; Majid, U.S. Pat. No. 5,070,081; Jarho, U.S. Patent Application Publication No. 2005/0153931; Hirayama (Advanced Drug Delivery Review 36 (1998) 125-141; and Watts (WO 99/32107) disclosed the preparation of cyclodextrin/cannabinoid complexes. Watts teaches adding THC to a soluble cyclodextrin in a biphasic oil-water mixture or in water. Majid teaches the formation of agglomerates by adding dissolved THC to a suspension of cyclodextrin and water and hexane. Jarho teaches adding THC and ethanol to cyclodextrin, adding water to dissolve the cyclodextrin, and recovering the precipitate.

Munjal (J. Pharm Sciences 95 11, Nov. 2006) teaches using an antioxidant and a basic pH microenvironment to stabilize THC.

SUMMARY OF THE INVENTION

The invention provides a compression molded solid dosage form for administration of a pharmaceutically active agent that is capable of being absorbed through oral mucosa. The invention also provides a direct compression formulation and a method of using the direct compression formulation to make a solid oral dosage form for administration of a pharmaceutically active agent that is absorbed through oral mucosa.

The direct compression formulation and solid oral dosage forms of this invention comprise a non-ionic polymeric solubility enhancer, a mucoadhesive polymer, a filler, a disintegrant, and a pharmaceutically active agent that is capable of being absorbed through oral mucosa. Conventional compression techniques may be employed for compressing the dry blend into a solid oral dosage form.

The invention provides, among other things, improved processes for making cannabinoid-cyclodextrin complexes and other complexes between a pharmaceutically active agent that can be dispersed in a liquid medium and complexed with cyclodextrin exhibiting enhanced stability, pharmaceutical formulations exhibiting improved stability, bioavailability and/or absorption of cannabinoids when administered, and dosage forms for administration of cannabinoids.

The improved processes of making cannabinoid-cyclodextrin complexes and other complexes generally involve dispersing at least one cannabinoid and suspending at least one cyclodextrin in a liquid medium to allow formation of a complex, and removing the liquid medium to provide a solid material containing the complex.

The formulations may comprise the above described complex(es) and at least one decomplexation agent.

Dosage forms in accordance with certain preferred embodiments of the invention include a complex dispersed in a matrix material comprising a hydrogel forming polymer.

These and other features, advantages and objects of the present invention will be further understood and appreciated by those skilled in the art by reference to the following specification and claims.

DETAILED DESCRIPTION OF PREFERRED EMBODIMENTS

The direct compression formulations used in preparing the pharmaceutical dosage forms of this invention are prepared by blending a non-ionic polymeric solubility enhancer, a mucoadhesive polymer, a filler, a disintegrant, and a pharmaceutically active agent that is capable of being absorbed through oral mucosa. The individual ingredients comprising the direct compression formulation and solid oral dosage forms of this invention are typically solid materials. However, one or more of the ingredients may be a semisolid or liquid material, provided that the resulting formulation is of a substantially solid character and is capable of being shaped into a solid oral dosage form by direct compression.

Non-ionic polymeric solubility enhancers that may be employed in the direct compression formulations and solid oral dosage forms of this invention include polyoxyethylene alkyl ethers; polyoxyethylene alkyl phenols; polyethylene glycol glycerol fatty acid esters; polyoxyethylene sorbitan fatty acid esters; polyoxyethylene-polyoxypropylene block copolymers; polyoxyethylene glycerides; polyoxyethylene sterols; polyoxyethylene vegetable oils; and polyoxyethylene hydrogenated vegetable oils. Preferred are polyoxyethylene-polyoxypropylene block copolymers. The expression "polyoxyethylene-polyoxypropylene block copolymer" refers to any block copolymer having at least one polyoxyethylene block and at least one polyoxypropylene block. Suitable polyoxyethylene-polyoxypropylene block copolymers are represented by the formula $HO-(CH_2-CH_2O-)_a-(CH_2-CH(CH_3)-O)_b-(CH_2-CH_2-O)_a-H$, wherein a is an integer of from 10 to 200 and b is an integer of 10 to 100. Suitable polyoxyethylene-polyoxypropylene block copolymers include a variety of commercially available products sold under various trade names, including Synperonic PE Series (ICI); Pluronic™ Series (BASF), Lutrol (BASF), etc. These polyoxyethylene-polyoxypropylene block copolymers are generically referred to as poloxamers. The block copolymer or other solubility enhancer may be present in the formulations and dosage forms of this invention in an amount of from about 1 to 30% by weight of the formulation or dosage form.

Mucoadhesive polymers which may be employed in the direct compression formulations and solid oral dosage forms of this invention include polyacrylic acid, which may or may not be partially cross-linked, sodium carboxymethyl cellulose, polyvinylpyrrolidone, polyvinyl alcohol, hydroxypropylcellulose, hydroxyethylcellulose and hydroxyethyl ethyl cellulose. Combinations of the above mucoadhesive polymers may also be employed. Other mucoadhesive polymers or combinations of mucoadhesive polymers may also be used. The mucoadhesive polymer may be present in an amount of from about 1 to 15% by weight of the formulation or dosage form.

Fillers that may be employed in the direct compression formulations and solid oral dosage forms of this invention include water-soluble saccharides such as lactose, mannitol, glucose, sucrose, dextrose, sorbitol, xylitol, and erythritol. Other water-soluble saccharides may also be employed and combinations of water-soluble saccharides may be used. Other fillers that may be employed include, with limitation, calcium sulfate, calcium carbonate, dibasic calcium phosphate, stearic acid, starch, and microcrystalline cellulose. The filler may be present in the formulations or dosage forms in an amount of from about 5 to 65% by weight of the formulation or dosage form.

The pharmaceutically active agent that may be used in the direct compression formulations and dosage forms of this invention include generally any pharmaceutically active agent that is capable of being absorbed through oral mucosa. Examples of pharmaceutically active agents that may be administered in an oral dosage form include hypnotics or sedatives such as diazepam and estazolam; antiepileptics such as meprobamate and nitrazepam; antipyretics; analgesics and anti-inflammatory agents such as acetaminophen; corticoids; psychoneurotropic agents such as chlorpromazine; anesthetics such as procanine and lidocaine; antihistamines such as diphenhydramine; cardiotonics such as digitalis; anti-arrhythmic agents such as pindolol and propranolol hydrochloride; diuretics such as theophylline, trichlormethiazide; vasoconstrictors such as dihydroergotamine mesylate and dihydroergotoxine mesylate; coronary vasodilators such as nitroglycerin; peripheral vasodilators such as inositol hexanicotinate; antiarteriosclerotic agents such as clofibrate; antitussives and expectorants such as ephedrine, codeine, dextromethorphan; peptic ulcer-treating agents such as famotidine, cimetidine and ranitidine; hormones and antihormones; antibiotics such as ampicillin and others. The pharmaceutically active agent may be prepared in an amount of from about 5 to 65% by weight of the formulation or dosage form.

An application of particular interest with respect to the invention is the administration of cannabinoids for various therapeutic applications, such as in the treatment of glaucoma, migraine headaches, spasticity, anxiety, analgesia, drug addiction and for the control of nausea and vomiting associated with chemotherapy and for appetite stimulation. The administration of cannabinoids such as $\Delta^9$-tetrahydrocannabinol (THC) via the buccal and/or sublingual route avoids hepatic first-pass metabolism. As is known in the art, when therapeutically active cannabinoids such as THC are administered orally, only about 10 to 20% of an administered dose reaches systemic circulation with highly variable maximal concentrations due to the combined effect of first pass hepatic metabolism and high lipid solubility. Desirably, to reduce the problems associated with high lipid solubility and low water-solubility, cannabinoids such as THC are incorporated into the solid oral dosage forms of this invention in the form of a cannabinoid-cyclodextrin complex. Examples of cyclodextrins (cyclic oligosaccharides consisting of $\alpha$-1,4-linked $\alpha$-D-glucopyranose units) include $\alpha$-cyclodextrin, $\beta$-cyclodextrin, $\gamma$-cyclodextrin, with $\beta$-cyclodextrin and water-soluble $\beta$-cyclodextrin derivatives being particularly preferred. Examples of $\beta$-cyclodextrin derivatives that may be employed include hydroxypropyl-$\beta$-cyclodextrin, sulfobutylether-$\beta$-cyclodextrin, maltosyl-$\beta$-cyclodextrin and methylated cyclodextrins, including dimethyl-$\beta$-cyclodextrin, trimethyl-$\beta$-cyclodextrin and randomly methylated $\beta$-cyclodextrin.

Formulations and solid oral dosage forms of this invention include disintegrating agents (disintegrants) such as sodium carboxylmethyl cellulose, crospovidone and the like in amounts sufficient to achieve a desirable and efficient disintegration rate that optimizes absorption of the pharmaceutically active agent, minimizes patient discomfort and inconvenience, or achieves a desired balance of absorption efficiency and reduced discomfort and/or inconvenience. Examples of suitable amounts of disintegrating agents, such as crospovidone (e.g., Polyplasdone XL, ISP) may range from about 2 to about 50% based on the weight of the direct compression formulation and/or oral dosage form.

The direct compression formulations and solid oral dosage forms of this invention may further comprise other optional ingredients as desired, including natural and/or artificial sweeteners such as aspartam, taste-masking agents and/or flavorants such as menthol, and colorants (e.g., red iron oxide dye). Glidants, lubricants such as magnesium stearate, and other processing aids may be employed as needed or desired to facilitate handling and/or compression into tablets or other oral dosage forms.

EXAMPLES

The following examples illustrate direct compression formulations, oral dosage forms and methods of preparing same in accordance with certain non-limiting aspects of the invention.

Two mucoadhesive formulations were developed for preparing solid oral dosage forms for buccal and/or sublingual administration of THC complex (e.g., a complex between THC and a cyclodextrin such as $\gamma$-cyclodextrin). The two formulations have the same ingredients, but in different amounts to achieve a different residence time on the oral mucosa. Specifically, the formulations shown in the following table have residence times of about 2 minutes and 10 minutes on the oral mucosa, respectively.

TABLE

| Ingredients | 2 minutes (%) | 10 minutes |
|---|---|---|
| THC Complex | 33.3 | 33.3 |
| Poloxamer, Lutrol 127 BASF | 6 | 6 |
| Menthol, A&C | 1.25 | 1.25 |
| Apartam, Amerisweet | 1.5 | 1.5 |
| Polyacrylic acid, Carbopol 71G. Noveon | 3 | |
| Dye, red iron oxide | 1.25 | 1.25 |
| Mannitol, Pearlitol 200SD, Roquette | 9 | 48.2 |
| Crospovidone, Polyplasdone XL, ISP | 44.2 | 5.0 |
| Mg Stearate, Mallickort | 0.5 | 0.5 |
| THC content | 1 mg | 1 mg |
| Tablet weight and size | 75 mg/10.0 mm | 75 mg/10.0 mm |

All of the ingredients listed in the above table, excluding the magnesium stearate lubricant, are blended together for about 5 minutes to form a dry particulate blend. Thereafter, the lubricant is added and the mixture is blended for about 2 more minutes. The above formulations may be compressed (such as in a conventional tablet pressing apparatus) employing a compression force of, for example, about 20-22 kN to form the desired solid oral dosage forms for buccal and/or sublingual administration. The dosage forms may be compressed into any of a variety of desirable tablet, wafer or pellet shapes, including relatively flat and thin dosage forms intended to enhance the surface area in contact with the oral mucosa.

The invention is generally directed to pharmaceutical complexes, including improved cannabinoid-cyclodextrin complex(es); pharmaceutical formulations and oral dosage forms comprising the improved complex(es), and optionally including a decomplexation agent; and dosage forms comprising a combination of the complex(es) and a mucoadhesive polymer that provides improved processing and/or improved characteristics such as those relating to disintegration and drug release profile.

The cannabinoid-cyclodextrin complexes generally exhibit improved stability as characterized by a reduced rate of degradation of the cannabinoid. Factors which contribute to the improved stability of the cannabinoid-cyclodextrin complexes include the use an antioxidant during preparation of the complex and/or preparation of the complex in an atmosphere having a very low oxygen content (e.g., less than 100 parts per million by volume (ppmv)). By employing an antioxidant and/or an atmosphere having a low oxygen content during preparation of the complex, degradation during complexation is substantially eliminated. Antioxidant that is not consumed during preparation of the complex can become associated with the complex and prevent or reduce subsequent degradation of the cannabinoid after the complex has been incorporated into a dosage form.

Use of a decomplexation agent external to the complex alters the strength of association between the active cannabinoid(s) and the cyclodextrin(s) and/or the rate of displacement, decomplexation, destabilization or dissociation of the cannabinoid(s) from the cannabinoid-cyclodextrin complex and, correspondingly alters the rate of release of the cannabinoid(s) from the dosage form after administration to a subject in need of treatment. The term "external" as used herein to describe the decomplexation agent means that the complexation agent is not a component of the complex. In certain embodiments, the decomplexation agent is added after the complex has been prepared.

Substantially any cannabinoid may be employed in preparing the complexes of this invention. Illustrative examples of cannabinoids that may be used include THC, cannabidiol (CBD), cannabinol (CBN), nabilone and combinations of thereof.

Although, cannabinoids are generally preferred, various cannabinoid derivatives and cannabinoid mimetics that are capable of binding with cannabinoid receptors in the body may be employed. Accordingly, endocannabinoids (e.g., molecules produced in the body which can bind to cannabinoid receptors), cannabinoid derivatives such as cannabidiolic acid (CBDA) (a substance that does not exert psychotropic or narcotic effects but possesses a variety of potentially useful pharmaceutical activities), and various cannabinoid mimetics may be employed. Thus, the expression "cannabinoid-cyclodextrin complex" is defined herein to encompass cannabinoid derivatives and cannabinoid mimetics, as well as cannabinoids themselves. Other examples of compounds that may be complexed with cyclodextrin to form the cannabinoid-cyclodextrin complexes of this invention include cannabigerols (CBGs), cannabichromenes (CBCs), cannabidiols (CBDs), cannabicyclol (CBL), cannabielsoin (CBE), and cannabitriol (CBT).

The terms "complexed, complexation, and a complex" as used to describe and claim the invention refer to a reversible interaction between the cannabinoid molecule(s) or other active ingredient and the cyclodextrin(s) that can be physical and/or chemical, and the formation of an entity comprised of a cyclodextrin or cyclodextrins and cannabinoid molecule(s) or other active ingredient. The term "cannabinoid-cyclodextrin complex" encompasses materials that have been generally referred to in the art and literature as cyclodextrin inclusion compounds or complexes, regardless of whether they actually are inclusion complexes. The term "decomplexation" refers to dissociation of the cannabinoid(s) from the cyclodextrin(s) and the resulting absence of interaction between the cannabinoid(s) and the cyclodextrin(s).

Cyclodextrins that are complexed with the cannabinoids in accordance with this invention include generally any cyclodextrin or combination thereof that are capable of being associated with a cannabinoid and result in an improved property selected from improved stability (i.e., a lower rate of degradation), higher product yields, higher water solubility and/or improved product uniformity. Examples of cyclodextrins that may be utilized in the invention include α-cyclodextrin, β-cyclodextrin, γ-cyclodextrin and β-cyclodextrin derivatives. Preferred cyclodextrins include, among others, γ-cyclodextrin and derivatives of β-cyclodextrin, including hydroxypropyl-β-cyclodextrin, hydroxyethyl-β-cyclodextrin, sulfoalkyl-β-cyclodextrin, ethylated β-cyclodextrin and methylated β-cyclodextrin.

The expression "antioxidant" as used to describe and claim certain embodiments of the invention refers generally to a chemical compound or substance that inhibits oxidation of a cannabinoid and/or a complex of a cannabinoid and a cyclodextrin. Antioxidants include compounds that react with and neutralize free radicals or chemicals that release free radicals and/or which otherwise stop, prevent or retard oxidation reactions that lead to or cause degradation of the cannabinoid in either its free or complexed form. Antioxidants that may be employed in the invention include pharmaceutically acceptable acids, especially pharmaceutically acceptable organic acids such as those selected from $C_2$-$C_{10}$ alkyl- or alkenyl-carboxylic acids having two or more carboxylic groups. Specific examples include malonic acid, succinic acid, fumaric acid, maleic acid, adipic acid, lactic acid, levulinic acid, sorbic acid, glutamic acid, aspartic acid, oleic acid, glutaric acid, tartaric acid, malic acid, ascorbic acid, and citric acid. Other antioxidants that can be used include butylated hydroxyanisole (BHA) and butylated hydroxytoluene (BHT), as well as other phenolic antioxidants.

The complex may be prepared in the presence of an antioxidant and/or antioxidant may be added after formation of the complex to inhibit oxidative degradation.

The term "decomplexation agent", as used to describe and claim certain embodiments of the invention, refers generally to a chemical compound or substance that, when present in an effective amount, alters the strength of association between the cannabinoid(s) and the cyclodextrin(s) and/or the rate of displacement, decomplexation, and/or destabilization of the complex or disassociation of the active cannabinoid molecule or molecules from the complex(es) once administered. Decomplexation agents include compounds or molecules that are capable of chemically adjusting the degree and/or strength of complexation and or association between the cyclodextrin(s) and the active molecule(s) and promote displacement of the active molecule(s) from the complex. The decomplexation agents facilitate decoupling of the cannabinoid from the cyclodextrin to improve bioavailability and absorption through mucosa (e.g., oral, rectal, vaginal) and/or through the gastrointestinal tract. Specific examples of decomplexation agents include, among others, malonic acid, succinic acid, fumaric acid, maleic acid, adipic acid, lactic acid, acetic acid, levulinic acid, sorbic acid, glutamic acid, aspartic acid, oleic acid, glutaric acid, tartaric acid, stearic acid, malic acid, ascorbic acid, and citric acid, hydroxyapatite, aspartame, dibasic calcium phosphate, monobasic calcium phosphate, sodium bicarbonate, potassium bicarbonate, calcium carbonate, inorganic salts, potassium carbonate other pharmaceutically active ingredients, carbonates, phenylalanine, water, calcium phosphate tribasic, potassium dibasic phosphate, potassium phosphate tribasic, bismuth subcarbonate, magnesium carbonate, iron subcarbonate, sodium phosphate dibasic, dihydroxyaluminium sodium carbonate, magnesium carbonate, propylene carbonate, zinc carbonate and sodium phosphate monobasic. Decomplexation agents that may be employed include molecules that have a greater tendency than the cannabinoid(s), once the dosage form has been administered, to occupy the immediate surroundings of the cyclodextrin(s), thereby forming a new complex with the cyclodextrin; molecules capable of altering the pH in the micro environment surrounding the cyclodextrin; and co-solvents and surfactants that have a higher affinity than the cyclodextrin(s) for the active(s) and thereby make it unfavorable for the active(s) to form a complex or complex(es). An amount of decomplexing agent that is suitable at generally effective ranges from about 0.01 to 19% by weight of the formulation or dosage form.

The cannabinoid(s)-cyclodextrin(s) complexes are prepared by dispersing a cannabinoid or cannabinoids, cyclodextrin(s), an optional surfactant, and an optional antioxidant or antioxidants in a liquid medium for a time sufficient to achieve a desired degree of complexation or chemical association between the cannabinoid and the cyclodextrin. More specifically, the cannabinoid(s) is (are) dissolved or suspended in the liquid medium and the cyclodextrin(s) is (are) suspended in the liquid medium. The terms "dissolved' and "suspended" are intended to have their ordinary meaning. Namely, the term "dissolved" is intended to mean that the cannabinoid is dispersed in the liquid at a molecular level, whereas the term "suspended" means that the cyclodextrin and optionally the cannabinoid is dispersed in the liquid medium in the form of fine particles supported by buoyancy. The cannabinoid(s), cyclodextrin(s), surfactant(s) and antioxidant(s) may generally be added in any order. However, it is desirable that the antioxidant or antioxidants are present in the liquid medium before or immediately after the cannabinoid(s) is (are) added. Optionally, the liquid medium containing the cannabinoid(s), cyclodextrin(s), surfactant(s) and antioxidant(s) may be agitated, either continuously or intermittently.

Examples of pharmaceutically acceptable surfactants that may be employed during preparation of the complex(es) include polyoxyethylene alkyl ethers; polyoxyethylene alkyl phenols; polyethylene glycol glycerol fatty acid esters; polyoxyethylene sorbitan fatty acid esters; polyoxyethylene-polyoxypropylene block copolymers; polyoxyethylene glycerides; polyoxyethylene sterols; polyoxyethylene vegetable oils; and polyoxyethylene hydrogenated vegetable oils.

After a time sufficient to form a desired degree of complexation or association between the cannabinoid(s) and the cyclodextrin(s), at least one binder or filler and at least one homogenizing agent may optionally be added and blended with the complex. The desired degree of complexation is depended on a variety of factors, including the particular cannabinoid(s) involved, the desired release profile and/or rate of release, the mode of administration, the ratio of the cyclodextrin to cannabinoid, and other factors. An appropriate degree of complexation can be determined by those of ordinary skill in the art employing routine experimentation. Following blending, the liquid medium may be removed to obtain a solid material containing the cannabinoid(s)-cyclodextrin(s) complex(es).

The term "solid material" as used herein refers to the material obtained after complexation and removal of the liquid medium, which is or includes matter that is more resistant to deformation and changes of volume than liquid or gaseous materials. More specifically, while the "solid material" may contain liquid or gaseous matter it is primarily composed of matter that has a higher Young's moldulus and/or shear modulus than liquids. Preferably, the "solid material" is comprised of finely divided particles that may be regarded as a powder or powder-like material. However, the term "solid material" is also intended to encompass other materials that can be handled like a powder or which have a substantial solid character, including semi-solid materials such as those having a dough-like or gelatin-like character.

Examples of liquid mediums that may be employed for preparing the cannabinoid(s)-cyclodextrin(s) complex(es) of the invention include organic solvents and/or non-aqueous solvents that may comprise one or more of a lower fatty acid ester, petroleum ether or hydrocarbon solvents such as cyclohexane, a halogenated hydrocarbon such as methylene chloride or chloroform, an aldehyde, a ketone, and an alcohol. Other suitable solvents include ethanol and propanol. However, other solvents or co-solvent systems in which cyclodextrin can be suspended or partially suspended and in which an effective amount of the cannabinoid can be dissolved may be employed. Typically, the liquid medium is removed by evaporation. However, other techniques such as micro filtration and lyophilization are contemplated.

In order to further inhibit oxidation during complexation, and to provide an improved, more homogeneous, consistent and pure product, substantially free of products of degradation, and which exhibit enhanced stability. The process for preparing the cannabinoid(s)-cyclodextrin(s) complex(es) is carried out in an atmosphere having a very low oxygen content (e.g., less than 100 ppmv). During such process, the liquid medium containing the cannabinoid(s) and cyclodextrin(s) is contacted with an atmosphere that is relatively inert with respect to oxidation of the cannabinoid(s). This may be accomplished by removing the oxygen in the atmosphere by using a replacement gas or gasses that may include nitrogen, neon, argon, xenon or similar inert gases or combinations of the gases. By employing a gas or combination of gases such as argon and or xenon that are heavier than air, a blanket is formed over the mixture and protects it against the introduction of oxygen, which could react with disassociated cannabinoid(s) in the liquid medium. Also, drying of the resulting complex can be done in a system that may be open, closed or a under a full or partial vacuum. The rate of solvent removal may be at a rate which allows completion of the reaction and higher yields. Because gases that are heavier do not diffuse as rapidly as air, the quantity of the heavier gas or gases used can be reduced as compared with lighter gases such as nitrogen.

Conventional ratios of cyclodextrin to cannabinoid may be employed during preparation of the complexes of the invention (e.g., from about 1 part by weight to about 10 parts by weight of cyclodextrin for 1 part by weight of cannabinoid). The antioxidant(s) may be employed in an amount from about 0.1 parts by weight to about 5 parts by weight per 1 part by weight of the cannabinoid(s). One or more of fillers, binders, disintegrants and or binder/filler-disintegrants (defined herein as excipients that are capable of functioning in a conventional sense as either a binder or filler, and also as a disintegrant, a specific example of a binder/filler-disintegrant being crospovidone) may be added to the liquid medium, preferably after substantial or complete complexation, in an amount effective to maintain a stable system during and/or after removal of the liquid medium. An amount of filler, binder, disintegrant and/or binder/filler-disintegrant that may be used is from about 0.1 parts by weight to about 1 part by weight per 1 part by weight of the resulting cannabinoid-cyclodextrin complex(es) on a dry basis.

Direct compression formulations used in preparing the dosage forms of this invention are capable of delivering pharmaceutically active molecules into the oral cavity in a controlled fashion that is capable of enhancing the absorption of the pharmaceutically active ingredient(s) through the oral mucosa. Such formulations may be prepared by blending (dispersing) the previously described cannabinoid-cyclodextrin complex(es) with a hydrogel-forming polymer. Other optional ingredients that may be incorporated (blended) into the formulation include non-ionic polymeric solubility enhancer(s), water soluble binder(s) and/or filer(s), and decomplexation agent(s). A disintegrant may also be employed. The individual ingredients comprising the direct compression formulation and solid oral dosage forms of this invention are typically solid materials. However, one or more of the ingredients may be a semisolid or liquid material, provided that the resulting formulation is of a substantially solid character and is capable of being shaped into a solid oral dosage form, as conventionally defined, by direct compression. The resulting compressed forms are, for example, suitable for use as buccal and/or sublingual oral dosage forms in which the cannabinoid-cyclodextrin complex(es) are dispersed in a matrix composed of a hydrogel forming polymer.

Solubility enhancers that may be employed in the direct compression formulations and solid oral dosage forms of this invention include non-ionic surfactants such as polyoxyethylene alkyl ethers; polyoxyethylene alkyl phenols; polyethylene glycol glycerol fatty acid esters; polyoxyethylene sorbitan fatty acid esters; polyoxyethylene-polyoxypropylene block copolymers; polyoxyethylene glycerides; polyoxyethylene sterols; polyoxyethylene vegetable oils; and polyoxyethylene hydrogenated vegetable oils. Preferred are polyoxyethylene sorbitol fatty acid esters such as polysorbate 80, and polyoxyethylene-polyoxypropylene block copolymers. The expression "polyoxyethylene-polyoxypropylene block copolymer" refers to any block copolymer having at least one polyoxyethylene block and at least one polyoxypropylene block. Suitable polyoxyethylene-polyoxypropylene block copolymers are represented by the formula HO—(CH$_2$—CH$_2$O—)$_a$—(CH$_2$—CH(CH$_3$)—O)$_b$—(CH$_2$—CH$_2$—O)$_a$—H, wherein a is an integer of from 10 to 200 and b is an integer of 10 to 100. Suitable polyoxyethylene-polyoxypropylene block copolymers include a variety of commercially available products sold under various trade names, including Synperonic PE Series (ICI); Pluronic™ Series (BASF), Lutrol (BASF), etc. These polyoxyethylene-polyoxypropylene block copolymers are generically referred to as poloxamers. The block copolymer or other solubility enhancer may be present in the formulations and dosage forms of this invention in an amount of from about 1 to 30% by weight of the formulation or dosage form. The non-iconic solubility enhancers improve bioavailability of decomplexed cannabinoids, providing enhanced absorption of hydrophobic cannabinoid compounds through oral mucosa. As an alternative, charged surfactants may be employed, such as sodium dilauryl sulfate, docusate sodium, etc.

The term mucoadhesive polymer is defined herein to encompass polymers that facilitate mucoadhesion by use of their specific properties. Examples of such properties include: high viscosity, high molecular weight, long chains, chain flexibility, spatial confirmation, optimum cross-linked density, optimum pH, and an optimum hydration potential. Mucoadhesive polymers can be considered as being of two broad classes: hydrophilic polymers and hydrogel forming polymers (hydrogels). Examples of hydrophilic polymers include carboxylic groups, poly vinyl pyrrolidone (PVP), methyl cellulose (MC), sodium carboxymethylcellulose (SCMC), hydroxypropylcellulose (HPC) and other cellulose derivative. Hydrogels can be classed as polymeric biomaterials that exhibit the basic characteristics of hydrogels, namely to swell by absorbing water, and interact with the mucus that covers epithelia by means of adhesion. Examples include polyacrylates, crosslinked modifications of polyacrylates, polyacrylate derivatives, chitosan, and chitosan derivatives.

Binders and/or fillers that may be employed in the direct compression formulations and solid oral dosage forms of this invention include lactose, mannitol, glucose, sucrose, sodium carboxymethyl cellulose, plasdone, hydroxypropyl methylcellulose, methyl cellulose, silicified microcrystalline methyl cellulose, xylitol, and erythritol. Other binders and fillers may be employed and combinations of binders and fillers may also be used. The binder(s) and/or filler(s) may be present in the formulations or dosage forms in an amount of from about 1% to 65% by weight of the formulation or dosage form.

An application of particular interest with respect to the invention is the administration of cannabinoids for various therapeutic applications, such as in the treatment of glaucoma, migraine headaches, spasticity, anxiety, pain, drug addiction and for the control of nausea and vomiting associated with chemotherapy and for appetite stimulation. The administration of cannabinoids such as $\Delta^9$-tetrahydrocannabinol (THC) via the buccal and/or sublingual route avoids hepatic first-pass metabolism, as is known in the art: when therapeutically active cannabinoids such as THC are administered orally, only about 10-20% of an administered dose reaches systemic circulation with highly variable maximal concentrations due to the combined effect of first pass hepatic metabolism and high lipid solubility. Desirably, to reduce the problems associated with high lipid solubility and low water-solubility, cannabinoids such as THC are incorporated into the solid oral dosage forms of this invention in the form of a cannabinoid-cyclodextrin complex. Once an interaction between the active and the cyclodextrin or cyclodextrins is formed the active is more stable, i.e., less prone to degradation in ambient conditions. In an in-vivo environment, the agent comes into contact or in proximity to the complex and increases the rate of dissociation of the cannabinoid(s) from the complex, thereby enhancing the bioavailability of the cannabinoid(s).

A significant advantage of the dosage forms of certain embodiments of this invention is that they facilitate enhanced absorption of the cannabinoid through oral mucosa and reduced ingestion of the cannabinoid. In the case of certain cannabinoids, such as THC, this means that there is considerably less oxidative degradation of the cannabinoid resulting in improved therapeutic effect with reduced psychotropic effect.

The direct compression formulations and solid oral dosage forms of this invention may further comprise other optional ingredients as desired, including natural and/or artificial sweeteners such as aspartame, taste-masking agents and/or flavors such as menthol, and colorants (e.g., red iron oxide dye). Glidants, lubricants such as magnesium stearate, and other processing aids may be employed as needed or desired to facilitate handling and/or compression into tablets or other oral dosage forms.

The following examples illustrate formulations, oral dosage forms and methods of preparing same in accordance with certain non-limiting aspects of the invention.

Example 1

A mucoadhesive formulation was developed for preparing solid oral dosage forms for buccal and/or sublingual administration of a mixture containing a cannabinoid and cyclodextrin involving first the preparation of a THC-γ-cyclodextrin complex. The formulation is shown in the following table.

TABLE

| Ingredient | Function | % |
|---|---|---|
| γ-Cyclodextrin | Complexing agent | 0.1-90.0 |
| Butylated Hydroxytoluene | Antioxidant | 0.00-10.00 |
| THC | Active substance | 0.01-10.00 |
| Ethanol | Solvent/suspension medium | 30.00-40.00 |
| Mannitol | Substrate | 0.00-50.00 |
| Polyethylene Glycol | Surfactant | 0.00-10.00 |

The γ-cyclodextrin, butylated hydroxytoluene, polyethylene glycol and THC are mixed together in a flask containing ethanol with 15 grams of glass beads (5-10 mm diameter) and the final blend is purged with argon. The flask is mounted on a rotary evaporator and rotated at 30 rpm for 24 hours. Mannitol is then added and well dispersed with agitation. A mild vacuum is applied until the mixture reaches a paste-like consistency. The resulting paste is completely dried by purging with a low flow argon over a 12 hour period.

The complex produced is then added to other excipients to give the final formulation:

TABLE

| Ingredients | Function | (%) |
|---|---|---|
| THC-Complex | complex | 1.00-90.00 |
| Sodium Bicarbonate | decomplexing agent | 0.00-10.00 |
| Menthol | taste masking agent | 0.00-10.00 |
| Sucralose | sweetener | 0.00-10.00 |
| Polyacrylic acid | mucoadhesive/hydrogel | 0.00-10.00 |
| Sorbitol | binder/filler | 0.00-50.00 |
| Mannitol | binder/filler | 0.00-50.00 |
| Isomalt sugar | binder/filler | 0.00-50.00 |
| Magnesium Stearate | lubricant | 0.00-0.50 |
| Poloxamer | solubility enhancer | 0.00-10.00 |
| Tablet weight and size | | 100 mg/7.0 mm |

All of the ingredients listed in the above table, excluding the magnesium stearate lubricant, are blended together for about 5 minutes to form a dry particulate blend. Thereafter, the lubricant is added and the mixture is further blended for about 2 more minutes. The above formulations may be compressed (such as in a conventional tablet pressing apparatus) employing a compression force of, for example, about 20-28 kN to form the desired solid oral dosage forms for buccal and/or sublingual administration. The dosage forms may be compressed into any of a variety of desirable tablet, wafer or pellet shapes, including relatively flat and thin dosage forms intended to enhance the surface area in contact with the oral mucosa.

Example 2

A mucoadhesive formulation was developed for preparing solid oral dosage forms for buccal and/or sublingual administration of a mixture containing cannabinoids and cyclodextrins involving first the preparation of a cannabinoid-cyclodextrin complex via wet granulation. The formulation is shown in the following table.

TABLE

| Ingredient | Function | % |
|---|---|---|
| γ-Cyclodextrin | Complexing agent | 0.1-10.0 |
| β-Cyclodextrin | Complexing agent | 0.1-10.0 |
| Butylated Hydroxyanisole | Antioxidant | 0.00-5.00 |
| Nabilone | Active substance | 1.00-10.00 |
| Cannabidiol | Active substance | 1.00-20.00 |
| Ethanol | Solvent/suspension medium | 1.00-50.00 |
| Acetone | Solvent/suspension medium | 1.00-50.00 |
| Polyvinyl povidone | Filler | 0.00-25.00 |
| Docusate Sodium | Anionic surfactant | 0.00-10.00 |

The γ-cyclodextrin, β-cyclodextrin, butylated hydroxyanisole, Nabilone and Cannabidiol are mixed in a flask containing ethanol and acetone using a magnetic stirring system, and the final blend is purged with argon and mixed for 24 hours. Docusate sodium and polyvinyl povidone are then added and well mixed with agitation. A mild vacuum is applied until the mixture reaches a paste-like consistency. The resulting paste is then dried by lyophilization.

A system comprising of the following excipients, in weight to weight percentages:

TABLE

| Ingredient | Function | % |
|---|---|---|
| Aspartame | taste masker | 1.0-2.5 |
| Aspartic Acid | Decomplexing agent | 1.5-5.0 |
| Polyacrylic acid | Mucoadhesive hydrogel former | 0.5-3.0 |
| Docusate Sodium | Anionic surfactant | 7.0-9.0 | and about 2.5% to about 90.0% of at least one member selected from the group consisting of mannitol, sorbitol and povidone (fillers, binders, and/or binder disintegrants), and the water soluble disintegrant dextrate, wherein the system is prepared by wet granulation and the resulting granule dried in a fluid bed.

The resulting granule is blended with the cannabinoid-cyclodextrin system, prepared as outlined above, for about 5 minutes, in the following ratios, to form a dry particulate blend:

a) about 10% to about 65% of complex; and
b) about 35% to about 90% of the granule system Thereafter, the lubricant, magnesium stearate, is added and the mixture and is blended in a total weight percentage of 0.5 to 1.0% for about 2 more minutes. The above formulations may be compressed (such as in a conventional tablet pressing apparatus) employing a compression force of, for example, about 15-28 kN to form the desired solid oral dosage forms for buccal and/or sublingual administration. The dosage forms may be compressed into any of a variety of desirable tablet, wafer or pellet shapes, including relatively flat and thin dosage forms intended to enhance the surface area in contact with the oral mucosa.

The above description is considered that of the preferred embodiment(s) only. Modifications of the invention will occur to those skilled in the art and to those who make or use the invention. Therefore, it is understood that the embodiment(s) shown in the drawings and described above are merely for illustrative purposes and not intended to limit the scope of the invention, which is defined by the following claims as interpreted according to the principles of patent law, including the doctrine of equivalents.

The invention claimed is:

1. A process for making a cannabinoid-cyclodextrin complex, comprising: dispersing a cannabinoid and suspending a cyclodextrin in a liquid medium for a time sufficient to form a cannabinoid-cyclodextrin complex; and removing the liquid medium to obtain a solid material containing the cannabinoid-cyclodextrin complex.

2. The process of claim 1, wherein a surfactant is added to the liquid medium.

3. The process of claim 1, wherein an antioxidant is added to the liquid medium.

4. The process of claim 1, wherein a surfactant and an antioxidant are added to the liquid medium.

5. The process of claim 1, wherein during complexation, the liquid medium containing the cannabinoid and the cyclodextrin is in an atmosphere having an oxygen content less than 100 parts per million by volume.

6. The process of claim 1, wherein during complexation, the liquid medium containing the cannabinoid and the cyclodextrin is in contact with an inert gas having an oxygen contact less than 100 points per million by volume.

7. The process of claim 6, wherein the inert gas is argon and/or zenon.

8. The process of claim 1, wherein at least one of a filler, binder, disintegrant or binder/filler-disintegrant is added to the liquid medium, the total amount of filler, binder, disintegrant as binder/filler-disintegrant added to the liquid medium being from about 0.1 parts to about 1 part by weight per 1 part by weight of the total of the cannabinoid(s) and the cyclodextrin(s) on a dry basis.

* * * * *